United States Patent [19]

Weiss

[11] Patent Number: 4,624,252
[45] Date of Patent: Nov. 25, 1986

[54] SURGICAL DEVICE

[76] Inventor: Sol Weiss, 17227 Quesan Pl., Encino, Calif. 91316

[21] Appl. No.: 701,916

[22] Filed: Feb. 14, 1985

[51] Int. Cl.⁴ ............................................. A61B 17/32
[52] U.S. Cl. ................................................. 128/305.3
[58] Field of Search ........................ 128/305.3, 200.26

[56] References Cited

U.S. PATENT DOCUMENTS 300,285  6/1884  Russell ............................ 128/325.3

Primary Examiner—Michael H. Thaler
Attorney, Agent, or Firm—Gerald L. Price

[57] ABSTRACT

An improved surgical device for performing thoracostomies and laparoscopies wherein the escape of air from the chest cavities or gas from the abdomen during such operations is prevented. The device includes a stylet holder wherein the holder includes needle halves having cooperating portions thereon for sealing off fluid flow when the portions are brought into contact. The stylet includes a needle having a bulged sharpened end adapted to seal off fluid flow so that fluid flows only through the needle. When the needle is withdrawn from between the needle halves, the needle halves are forced apart then mate so that the cooperating portions engage and seal off fluid flow.

1 Claim, 4 Drawing Figures

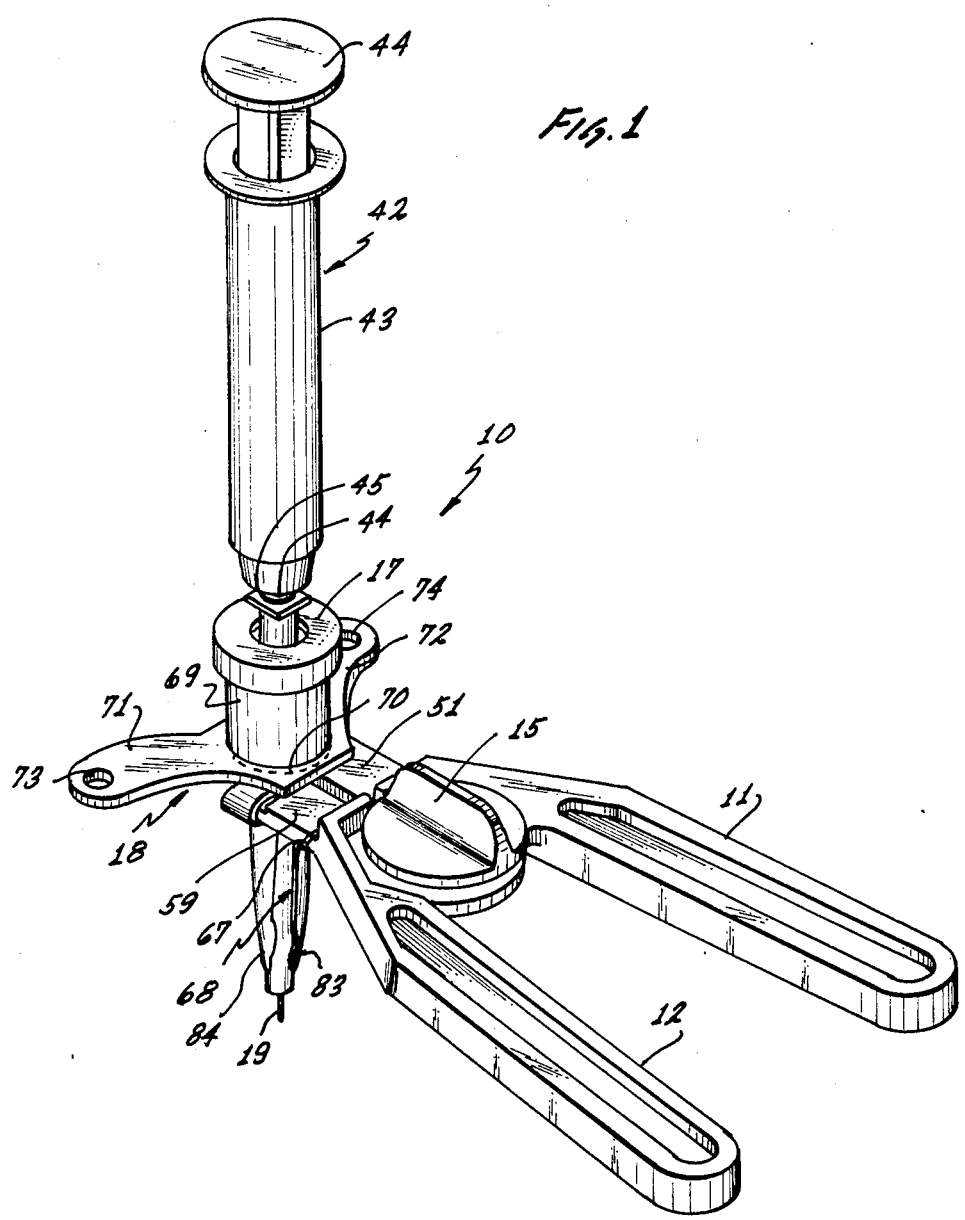

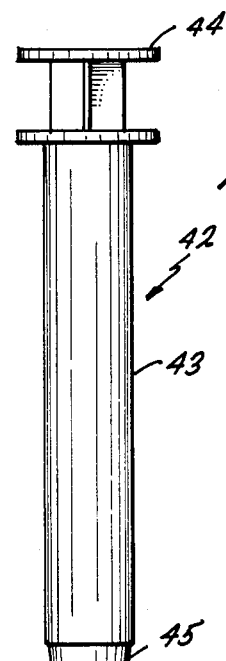
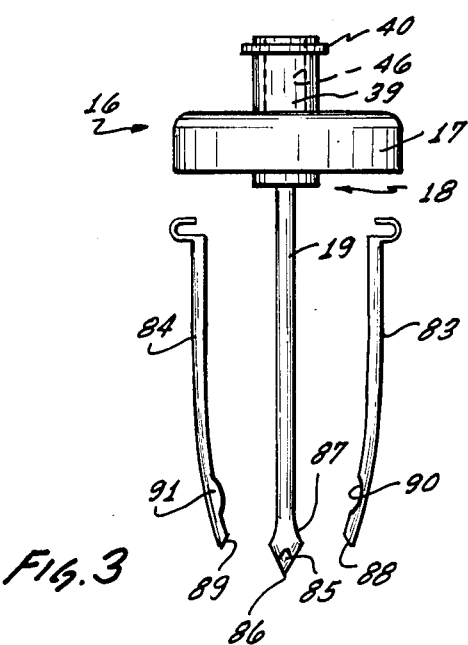
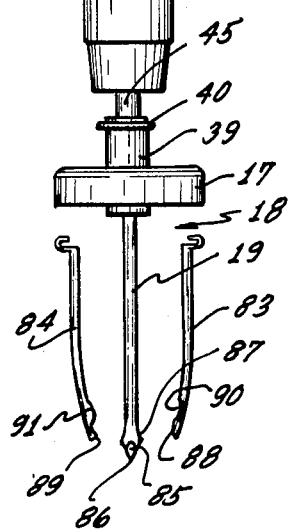
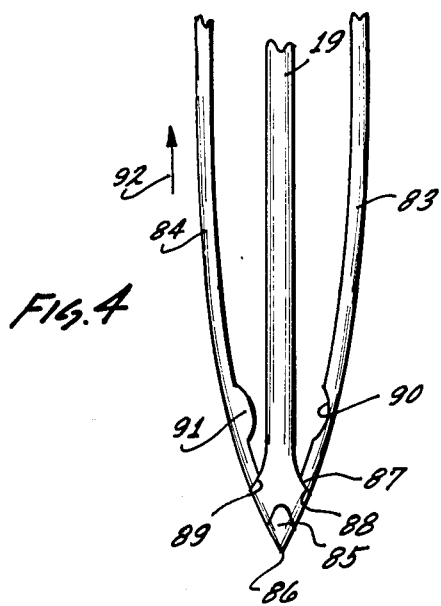

SURGICAL DEVICE

BACKGROUND OF THE INVENTION

1. Field of the Invention

The invention relates to surgical devices; and, more particularly, to an improved stylet and needle for performing thoracostomies and laparoscopies.

2. Description of the Prior Art

In my copending application Ser. No. 701,914, filed Feb. 14, 1985 I disclose an improved surgical device for performing emergency cricothyrotomies/tracheotomies, thoracostomies and laparoscopies. The device includes a holder for a stylet or tube which holder includes a two-part needle attached to a pair of handles, each handle including one part of the needle, which handles can be spread apart for insertion of a tube or stylet between the needle parts. The tube or stylet is then held between the needle parts. When it is desired to remove the device from the patient, one of the handles having its needle part can be removed from the other handle having its needle part without disturbing the tube or stylet held between the needle parts. In this manner, sutures can be easily made around a chest or throat opening in which the device has been inserted since only the tube remains in place.

There is a need for improved surgical instruments for performing thoracostomies since, in this operation, negative air pressure in the chest cavities creates special problems. In such operations, it is difficult to remove the trocar and chest tube. The flesh or walls of the puncture grasps the chest tube and makes it difficult to remove the holder for the tube so that the wound surrounding the tube can be sutured. There is thus a need for an improved surgical device for performing thoracostomies where the holder for the tube can be easily removed without the need for removing or disturbing the tube.

In laparoscopies, gas added into the abdomen for the purpose of separating the abdomen wall from the intestines to carry out the operation creates special problems. In this case, there is also a need for closing off the release of gas when the stylet is removed from the needle halves. Such removal with conventional stylets and needle halves could result in the undesired release of gas from the abdomen cavity.

Thus, there is a need for an improved surgical instrument that is useful in both laparoscopies and thoracostomies where the escape of air from the chest cavities or gas from the abdomen is prevented.

SUMMARY OF THE INVENTION

It is an object of this invention to provide an improved surgical device particularly suited to performing laparoscopies and thoracostomies.

It is a further object of this invention to provide an improved stylet and needle particularly suited to performing thoracostomies and laparoscopies.

These and other objects are preferably accomplished by providing a device which includes a stylet holder wherein the holder includes needle halves having cooperating portions thereon for sealing off fluid flow when the portions are brought into contact. The stylet includes a needle having a bulged sharpened end adapted to seal off fluid flow so that fluid flows only through the needle. When the needle is withdrawn from between the needle halves, the needle halves are forced apart then mate so that the cooperating portions engage and seal off fluid flow.

BRIEF DESCRIPTION OF THE DRAWING

FIG. 1 is a vertical view of an improved surgical device in accordance with the teachings of the invention;

FIG. 2 is a vertical view of a portion of the device of FIG. 1;

FIG. 3 is a detailed view of the lower portion of the device of FIG. 2; and

FIG. 4 is an enlarged view of the needle halves and stylet needle alone of the device of FIGS. 1 to 3.

DESCRIPTION OF THE PREFERRED EMBODIMENT

An improved holder for a stylet and airways is disclosed in my copending application Ser. No. 701,914, filed Feb. 14, 1985 the teachings of which are incorporated herein by reference. In that application, I disclose a holder which can be separated into two parts, each part carrying a needle half and adapted to hold therebetween a stylet and/or airway. In this application, I disclose a similar holder but it is to be understood that any suitable holder may be used and it need not be separable, as disclosed in my copending application, as long as the holder has separate needle halves that clasp or clamp a stylet or airway therebetween. Reference should be made to my copending application for a complete understanding of the holder illustrated herein.

Thus, as seen in FIG. 1, device 10 includes a locking key 15 inserted into aligned openings (not visible) in handle portions 11,12 and band 67 is encircled about extension portions 51,59. Syringe 42, with obturator 44, is joined to the stylet 18 (see also FIGS. 2 and 3) as will be discussed. Needle 19 is inserted into a conventional tube 68 which is clasped between needle halves 83,84, as shown. Tube 68 has an upper cylindrical portion 69 and a lower cylindrical portion 70, portion 69 being greater in diameter than portion 70 with a throughbore therebetween. Flanges 71,72 extend from opposite sides of portion 69 at the intersection thereof with lower portion 70, and each flange is apertured, at aperture 73,74, for securing via linear elements in apertures 73,74, tube 68 to the patient.

A conventional syringe 42 having a cylindrical main body 43 and obturator 44 is shown as assembled to collar 17 and stylet 18 (FIG. 2). As seen, the lower end of cylindrical main body 43 terminates in a cylindrical end 45 which is adapted to be inserted into the opening 46 through flange 40 on boss 39 and therethrough (see also FIG. 3). In this manner, a conventional syringe is quickly and easily assembled to the device 10.

Stylet holder 16 (FIG. 3) is provided with a collar 17 adapted to receive therein a stylet 18 having a conventional hollow needle 19 included therewith.

As discussed in my copending application Ser. No. 701,914, the device disclosed therein, and the holder 10 of FIG. 1 herein, may be used to perform thoracostomies and laparoscopies. In such operations, negative air pressure in the chest cavities, and gas added into the abdomen for the purpose of separating the abdomen wall from the intestines to carry out the operation, create special problems. In these cases, there is a need for closing off the escape or air or release of gas when the stylet is removed from between the needle halves. For example, as discussed in my copending application Ser. No. 701,914, the stylet 77 of FIG. 29 is removed from between the needle halves 78,79. This could result in the undesired escape of air from the chest cavities or release of gas from the abdomen cavity.

Thus, as shown in FIGS. 1 to 3, straight needle halves 83,84 are shown with stylet needle 19 inserted between halves 83,84 when such halves are held together via handle portions 11,12 and related structure. However, the terminal end of stylet needle 19, which of course is hollow and has a terminal opening 85 at its sharpened end 86, is flared or bulged outwardly at 87 to form a peripheral outer enlarged surface. The needle halves 83,84 are also conventional terminating in sharp ends 88,89 and of course configured internally as needle halves 13,14 in my copending application Ser. No. 710,914, the teachings of which are incorporated herein by reference, but include a concave portion 90 on the inner wall of one of the needle halves, such as needle half 83, and a convex portion 91 on the other needle half, such as needle half 84. Convex portion 91 is adapted to receive therein concave portion 90 in substantially a fluid tight manner. It can be appreciated that the bulged surface 87 of needle stylet 19 abuts against the ends 88,89 when stylet needle 19 is inserted between needle halves 83,84. This engagement stops the flow of air back out of the chest cavity or escape of gas from the abdomen cavity. However, when stylet needle 19 is removed from between halves 83,84, in the direction of arrow 92, the halves part to allow removal, then move together with convex surface 91 entering concave surface 90 again sealing off air or gas flow. In this manner, an improved stylet and needle is disclosed which can be utilized with the device disclosed in my copending application Ser. No. 701,914 or with any suitable holder wherein the needle halves are modified as herein disclosed to perform improved thoracostomies and laparoscopies.

I claim:

1. In a surgical instrument including a holder for a stylet wherein said holder includes a pair of extension portions having said stylet held therebetween and having a generally semi-circular opening therethrough and a straight needle half secured to each extension portion extending down from said semi-circular opening and each of said needle halves having an inner groove terminating at their terminal ends in sharp edges, each of said grooves being aligned with its respective semi-circular opening so that, when said extension portions abut against each other, said needle halves form a generally circular channel communicating at one end with the exterior of said extension portions and at the other end with said sharp edges, said stylet including a straight hollow needle extending downwardly between said needle halves, the improvement which comprises:

said stylet needle extending below the terminal ends of said needle halves when said stylet is retained between said extension portions, said needle terminating in a sharp end having a bulged portion abutting against the terminal ends of said needle halves so that fluid cannot flow between said sharp end and said terminal ends, said needle halves having cooperating means thereon adjacent said terminal ends preventing fluid flow through said needle halves when said needle is removed from between said needle halves, said cooperating means including one of said needle halves having a concave portion therein between said extension portion and said terminal end adjacent said terminal end and the other of said needle halves having a convex portion therein between said extension portion and said terminal end adjacent said terminal end, said convex portion mating with said concave portion to seal off fluid flow.

* * * * *